(12) United States Patent
Shaw et al.

(10) Patent No.: US 9,528,969 B2
(45) Date of Patent: Dec. 27, 2016

(54) APPARATUS, SYSTEM AND METHOD FOR FLASH HEATING

(71) Applicant: MORPHO DETECTION, INC., Newark, CA (US)

(72) Inventors: Bradley Douglas Shaw, Plaistow, NH (US); Lyndon Karl Goedecke, Everett, MA (US)

(*) Notice: Subject to any disclaimer, the term of this patent is extended or adjusted under 35 U.S.C. 154(b) by 401 days.

(21) Appl. No.: 14/103,061

(22) Filed: Dec. 11, 2013

(65) Prior Publication Data

US 2015/0163857 A1    Jun. 11, 2015

(51) Int. Cl.
| | |
|---|---|
| *G01N 33/00* | (2006.01) |
| *G01N 1/02* | (2006.01) |
| *G01N 1/22* | (2006.01) |
| *G01N 1/40* | (2006.01) |
| *H05B 3/24* | (2006.01) |

(52) U.S. Cl.
CPC ............ *G01N 33/0011* (2013.01); *G01N 1/02* (2013.01); *G01N 1/2214* (2013.01); *G01N 1/405* (2013.01); *H05B 3/24* (2013.01); *G01N 2001/022* (2013.01); *G01N 2001/028* (2013.01); *G01N 2001/4027* (2013.01); *H05B 2203/003* (2013.01); *H05B 2203/037* (2013.01)

(58) Field of Classification Search
CPC .............................. G01N 1/02; G01N 33/0011
USPC ........................................................ 73/23.2
See application file for complete search history.

(56) References Cited

U.S. PATENT DOCUMENTS

| 5,928,549 A | 7/1999 | Hitzigrath |
| 6,301,960 B1 * | 10/2001 | Yamakawa ............ G01F 1/6845 73/204.26 |
| 2008/0217524 A1 * | 9/2008 | Mawer ..................... G01N 1/02 250/281 |
| 2010/0126284 A1 * | 5/2010 | Boudries ................ G01N 1/405 73/863.12 |

FOREIGN PATENT DOCUMENTS

| DE | 2045725 A1 | 3/1972 |
| DE | 2524840 A1 | 8/1976 |
| EP | 1584912 A1 | 10/2005 |
| GB | 2322273 A | 8/1998 |
| JP | S60236029 A | 11/1985 |
| JP | 2005050626 A * | 2/2005 |

OTHER PUBLICATIONS

Extended European Search Report, dated Apr. 10, 2015, for co-pending EP patent application No. EP 14004012.2 (10 pgs.).
EP Communication, dated Aug. 23, 2016, for co-pending EP patent application No. EP 14004012.2 (7 pgs.).

* cited by examiner

*Primary Examiner* — Clayton E Laballe
*Assistant Examiner* — Dennis Hancock
(74) *Attorney, Agent, or Firm* — Armstrong Teasdale LLP

(57) ABSTRACT

A flash heater element includes a first surface having a central region and an electrical flow path disposed on the first surface. The electrical flow path includes a central portion disposed at least partially within the central region and a peripheral portion disposed peripherally outwardly from the central region. A width of the electrical flow path is greater within at least a portion of the central portion than within the peripheral portion.

19 Claims, 7 Drawing Sheets

APPARATUS, SYSTEM AND METHOD FOR FLASH HEATING

BACKGROUND

The field of the invention relates generally to apparatus, systems, and methods for trace detection, and more particularly, to thermal desorption of trace particles to facilitate detection.

Some known detection systems detect trace materials from a swab that is used to sample trace particles from luggage, clothing, or other sources of trace particles. The swab is inserted into a small heated desorber, and the heat from the desorber changes the phase of the sampled trace particles from solid to vapor. The vapor is then channeled into a detector, which analyzes the chemical and/or biological composition of the vapor.

At least some known detection systems incorporate flash heating to vaporize trace particles. Some known flash heaters include one or more planar foil heating elements, each of which is etched to form a serpentine conducting path of essentially constant width. The conductive path is generally designed to have low resistance and a large width relative to its thickness to facilitate an increased heat output. The temperature of such etched-foil flash heater elements can increase by, for example, approximately 100 degrees Celsius or more in a few seconds.

At least some known detection systems use such a flash heater to quickly step a desorber from a first temperature, corresponding to a vaporization temperature of a first trace material of interest, to a second temperature, corresponding to a vaporization temperature of a second trace material of interest. However, such rapid flash heating typically causes some locations of the heating element surface to heat more quickly than others, causing localized hot spots and large temperature gradients across the heating element surface. Collected trace particles on portions of the swab adjacent to relatively hot or cool spots on the heating element may not vaporize within an expected time period or may degrade too quickly, resulting in decreased quality and consistency of detection.

At least some known heating elements suitable for flash heaters have attempted to limit non-uniformity in the temperature of the heating element by limiting an effect termed "current crowding." Current crowding refers to the tendency for electrical currents, which follow the path of minimum resistance, to crowd around the inside of each bend in a serpentine foil heating element, similar to runners taking the shortest path around a curve on a track. Thus, current crowding creates relatively hot spots around the inside of the bends and relatively cool spots around the outside of the bends. Some known heating elements have attempted to limit the temperature gradient across the bend by etching a single, relatively wide serpentine foil element into multiple parallel narrower elements, distributing the current crowding effect among each parallel current path. However, this attempt to limit current crowding does not mitigate other factors that lead to a large temperature gradient across known serpentine etched-foil heating elements. One such factor is that the peripheral edges of the foil heating element are free to transfer heat to the environment in directions both normal to the foil surface and tangential to the foil surface, while the inner portions of the heating element can only transfer heat to the environment in a direction normal to the foil surface. As a result, a large temperature gradient may develop between the relatively hotter center of the element and the relatively cooler periphery of the element when the flash heater is activated.

BRIEF SUMMARY

In one aspect, a flash heater element is provided. The flash heater element includes a first surface having a central region and an electrical flow path disposed on the first surface. The electrical flow path includes a central portion disposed at least partially within the central region and a peripheral portion disposed peripherally outwardly from the central region. A width of the electrical flow path is greater within at least a portion of the central portion than within the peripheral portion.

In another aspect, a detection system is provided. The detection system includes a housing having a slot configured to receive a sampling device. The detection system also includes a desorber disposed within the housing proximate the slot. The desorber includes a receptacle aligned with the slot, the receptacle configured to receive at least a portion of the sampling device. The detection system further includes at least one heater disposed within the housing external to the receptacle, the at least one heater operable to maintain the receptacle at a first temperature such that, when the sampling device is inserted into the receptacle, a first class of trace particles collected on the sampling device is vaporized. The detection system further includes a flash heater element including a first surface having a central region and an electrical flow path disposed on the first surface. The electrical flow path includes a central portion disposed at least partially within the central region and a peripheral portion disposed peripherally outwardly from the central region. A width of the electrical flow path is greater within at least a portion of the central portion than within the peripheral portion. The flash heater element is configured to increase the receptacle to a second temperature such that a second class of trace particles collected on the sampling device is vaporized. Additionally, the detection system includes a detector disposed within the housing in flow communication with the desorber. The detector is configured to receive and identify the vaporized first class of trace particles and the vaporized second class of trace particles.

In yet another aspect, a method of making a flash heater element is provided. The method includes forming a first surface having a central region and forming an electrical flow path on the first surface. Forming the electrical flow path includes forming a central portion at least partially within the central region and forming a peripheral portion peripherally outwardly from the central region, such that a width of the electrical flow path is greater within at least a portion of the central portion than within the peripheral portion.

BRIEF DESCRIPTION OF THE DRAWINGS

Non-limiting and non-exhaustive embodiments are described with reference to the following figures, wherein like reference numerals refer to like parts throughout the various views unless otherwise specified.

DETAILED DESCRIPTION OF THE INVENTION

Figure 1:
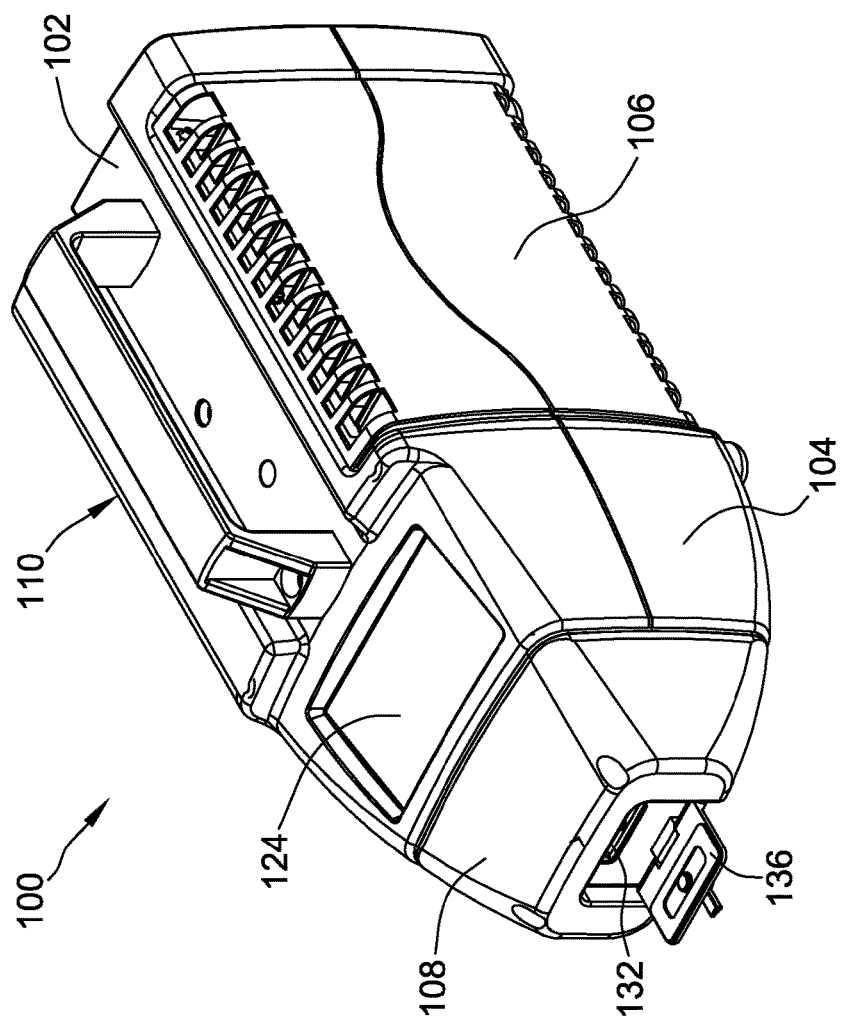
FIG. 1 is a perspective view of an exemplary detection system.
Figure 2:
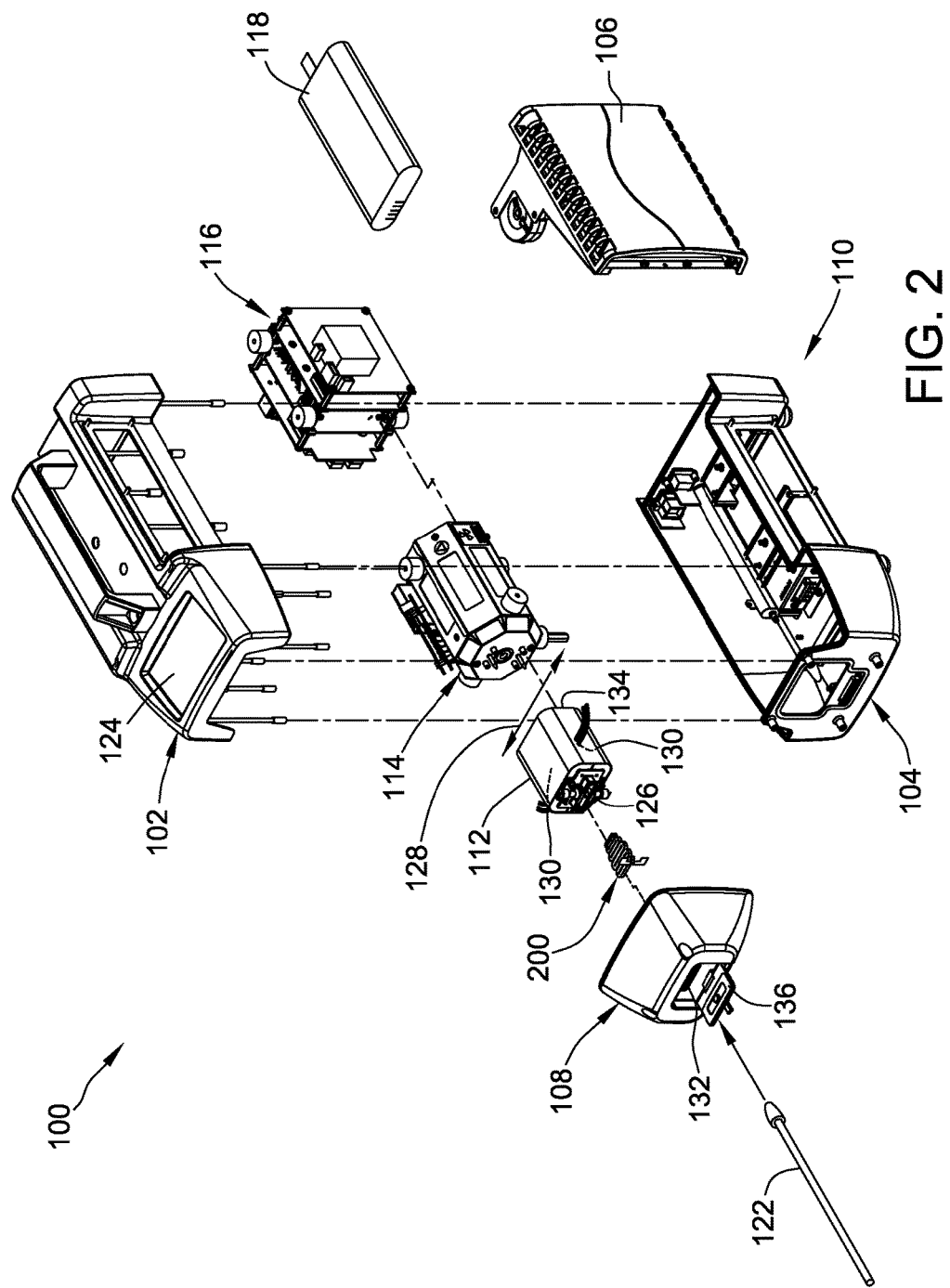
FIG. 2 is an exploded isometric view of the exemplary detection system shown in FIG. 1.

FIG. 1 is a perspective view, and FIG. 2 is an exploded isometric perspective view, of an exemplary detection system 100 configured to assess the chemical composition and/or biological nature or identity of an unknown substance or material to facilitate identifying potential chemical threats and/or potential biological threats. In the exemplary embodiment, detection system 100 is a portable device. In certain embodiments, detection system 100 may be a handheld device. Alternatively, detection system 100 may be any size.

With reference to FIG. 1 and FIG. 2, in the exemplary embodiment, detection system 100 includes a top housing assembly 102, a bottom housing assembly 104, a side panel assembly 106, and a front nose assembly 108 configured to be coupled together to form a housing 110 for the system. A door 136 in front nose assembly 108 can be opened to provide access to a slot 132. Disposed within housing 110 are a desorber 112, a detector 114, an electronics assembly 116, and a power source 118. In the exemplary embodiment, power source 118 is a rechargeable battery or the like.

A user interface 124, for example a touch-screen LCD display, may be disposed on housing 110, for example, on top housing assembly 102. User interface 124 is operatively coupled to electronics assembly 116 and is configured to allow a user to input commands into, and view results from, detection system 100. In turn, electronics assembly 116 is operatively coupled to desorber 112 and detector 114 to control their operation in accord with user commands.

Detector 114 is coupled in flow communication with desorber 112. More specifically, detector 114 is configured to receive vapor from desorber 112 and analyze its composition. In some embodiments, vapor is channeled from desorber 112 into detector 114 by a carrier gas. In alternative embodiments, other known methods of channeling vapor from desorber 112 into detector 114 may be used. Detector 114 may analyze the components of the vapor using one or more methods such as ion mobility spectrometry, ion trap mobility spectrometry, gas chromatography, mass spectrometry, and/or any other suitable detector technology. In the exemplary embodiment, detector 114 is configured to identify vapors associated with at least conventional explosives or homemade explosives. In alternative embodiments, detector 114 also may be configured to identify vapors associated with chemical or biological weapon agents, toxic industrial compounds, illicit drugs, and/or other substances of interest. The results of the composition analysis from detector 114 may be displayed via user interface 124 and/or stored by electronics assembly 116.

In the exemplary embodiment, desorber 112 is disposed in housing 110 proximate front nose assembly 108. Desorber 112 is configured to receive at least a portion of a sampling device 122. More specifically, desorber 112 includes a receptacle 126 configured to align with slot 132 in front nose assembly 108 such that at least a portion of sampling device 122 may be inserted through slot 132 and received into receptacle 126. Trace particles for analysis are collected on sampling device 122, for example by swabbing luggage, clothing, and/or other surfaces of interest, prior to insertion of sampling device 122 into desorber 112. Sampling device 122 may be, for example, a swab, a cartridge-shaped sampling trap, or any other suitable sampling device.

In some embodiments, at least one heater 130 is disposed external to receptacle 126. Heaters 130 may be coupled to desorber 112, or alternatively disposed within housing 110 proximate desorber 112. Heaters 130 are configured to set receptacle 126 to a first temperature, and to maintain receptacle 126 at the first temperature in a steady-state condition. For example, each heater 130 may be an electrical resistance heater operated at a constant power load, and aluminum plates (not shown) may be used to spread the heat uniformly across the surface of desorber 112. Electronics assembly 116 may receive temperature feedback from desorber 112 and may adjust the power supplied to each heater 130 to facilitate maintaining the first temperature in a steady-state condition. In some embodiments, the first temperature may be chosen based on a vaporization temperature of a first substance, or a first class of substances, of interest. In a particular embodiment, the first temperature is within a range of about 220 to about 245 degrees Celsius.

Additionally, in certain embodiments, detection system 100 includes a flash heater element 200. In the exemplary embodiment shown in FIG. 3, flash heater element 200 includes a first surface 202, a second surface 204, and a bridge tab 206 intermediate, and electrically coupled to each of, first surface 202 and second surface 204. An inlet 212 is defined between an inlet edge 214 of first surface 202 and an inlet edge 216 of second surface 204. Bridge tab 206 is electrically coupled between a second edge 224 of first surface 202, opposite first surface inlet edge 214, and a second edge 226 of second surface 204, opposite second surface inlet edge 216. Second edges 224 and 226 define a second end 228 of flash heater element 200 opposite inlet 212.

Each of first surface 202 and second surface 204 is an etched metallic surface that is configured to be electrically coupled to a power source, such as power source 118 (shown in FIG. 2), and to use resistive heating to increase in temperature and transmit a heat output. Thus, an electrical flow path 220 is defined on first surface 202, and an electrical flow path 222 is defined on second surface 204. Moreover, in the exemplary embodiment, a first connecting tab 208 is electrically coupled to first surface 202, and a second connecting tab 210 is electrically coupled to second surface 204. Thus, in the exemplary embodiment, electrical flow path 220 and electrical flow path 222 are connected in series from first connecting tab 208 through first surface 202, bridge tab 206, and second surface 204, to second connecting tab 210.

In the exemplary embodiment, flash heater element 200 is fabricated unitarily from a nickel-iron alloy, such as for example INVAR® (Aperam Alloys Imphy of Montargis, France), and is etched to include first connecting tab 208, first surface 202, bridge tab 206, second surface 204, and second connecting tab 210. Alternatively, flash heater element 200 may be fabricated from any alloy foil having a low thermal mass that facilitates rapid heating of first surface 202 and second surface 204, and that enables desorber 112 to function as described herein. Also, in alternative embodiments, any of first connecting tab 208, first surface 202, bridge tab 206, second surface 204, and second connecting tab 210 may be formed separately from one or more components, and/or first surface 202 and second surface 204 may be configured for operable coupling to separate electrical circuits, rather than to a single circuit.

Figure 3:
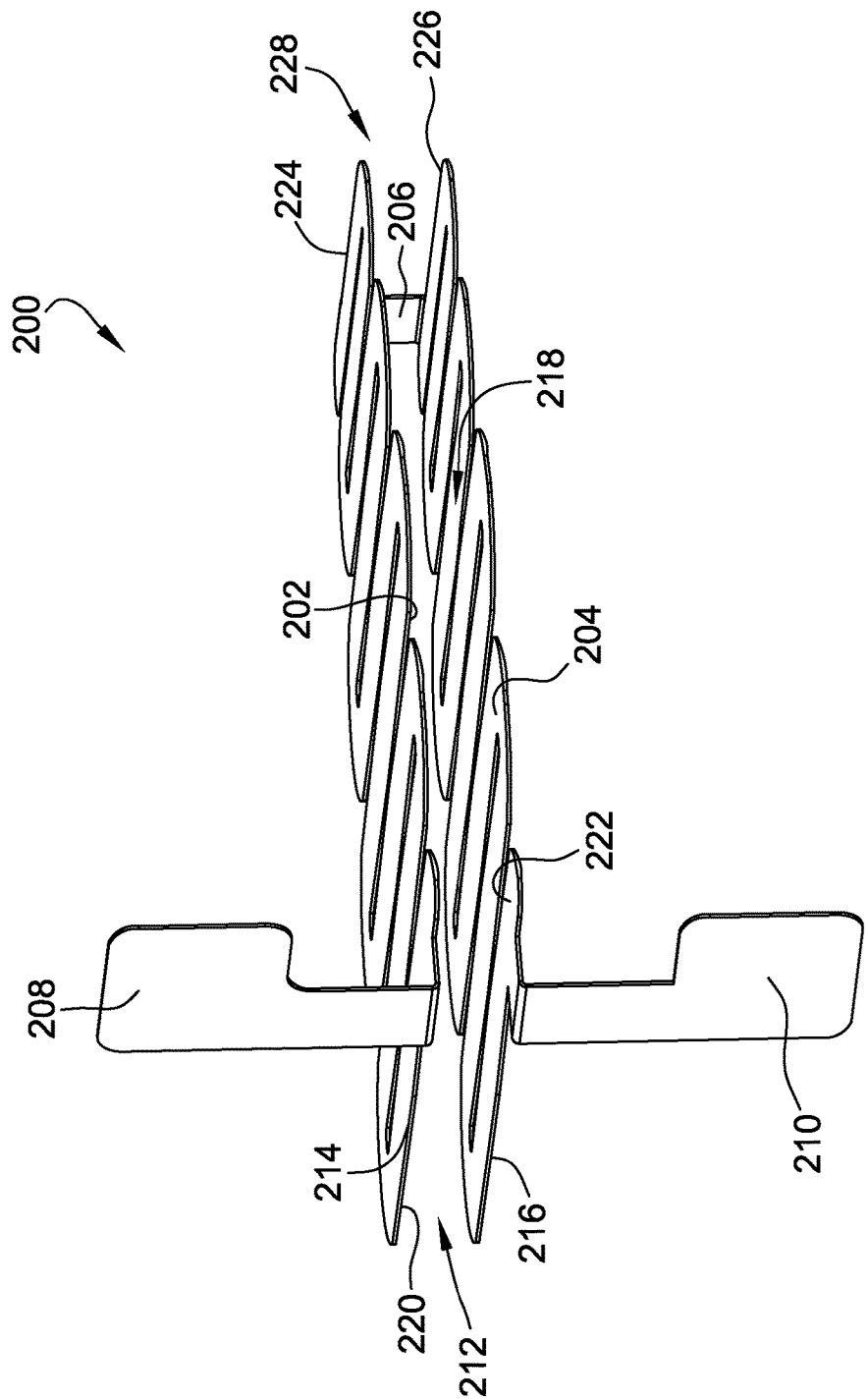
FIG. 3 is a perspective view of an exemplary flash heater element that may be used with the exemplary detection system shown in FIG. 1 and FIG. 2.

With reference to FIG. 2 and FIG. 3, in the exemplary embodiment, flash heater element 200 is disposed within desorber 112. More specifically, flash heater element 200 is oriented within desorber 112 such that first surface 202 and second surface 204 respectively at least partially define first and second opposite sides of receptacle 126. Moreover, inlet 212 aligns with slot 132 such that at least a portion of sampling device 122 may be inserted through slot 132, through inlet 212, and into receptacle 126. In other words, when sampling device 122 is inserted into detection system 100, at least a portion of sampling device 122 is positioned within an interior region 218 defined between first surface 202 and second surface 204.

First surface 202 and second surface 204 are retained on opposite sides of receptacle 126 by any suitable retention hardware, such as by coupling each of first surface 202 and second surface 204 to a frame element and a retention plate (not shown). First surface 202 and second surface 204 are oriented such that when power is applied to flash heater element 200, first surface 202 and second surface 204 each emit heat into interior region 218. Thus, first surface 202 and second surface 204 cooperate to increase a temperature within interior region 218 when power is applied to flash heater element 200.

In some embodiments, flash heater element 200 is configured to increase a temperature within receptacle 126 to a second temperature that is greater than the first temperature. Moreover, in certain embodiments, flash heater element 200 is configured to increase the temperature to the second temperature in a relatively short time period, such as less than approximately 5 seconds. In a particular embodiment, flash heater element 200 is configured to increase the temperature within receptacle 126 to the second temperature in less than approximately 2 seconds. The second temperature may be chosen based on a vaporization temperature of a second substance, or a second class of substances, of interest. In a particular embodiment, the second temperature is within a range of about 350 to about 450 degrees Celsius. Moreover, in some embodiments, electronics assembly 116 is programmed to operate flash heater element 200 to increase the temperature within receptacle 126 to each of a plurality of temperatures in sequence, where each of the plurality of temperatures is chosen based on a vaporization temperature of a corresponding one of a plurality of substances, or classes of substances, of interest.

Figure 4:
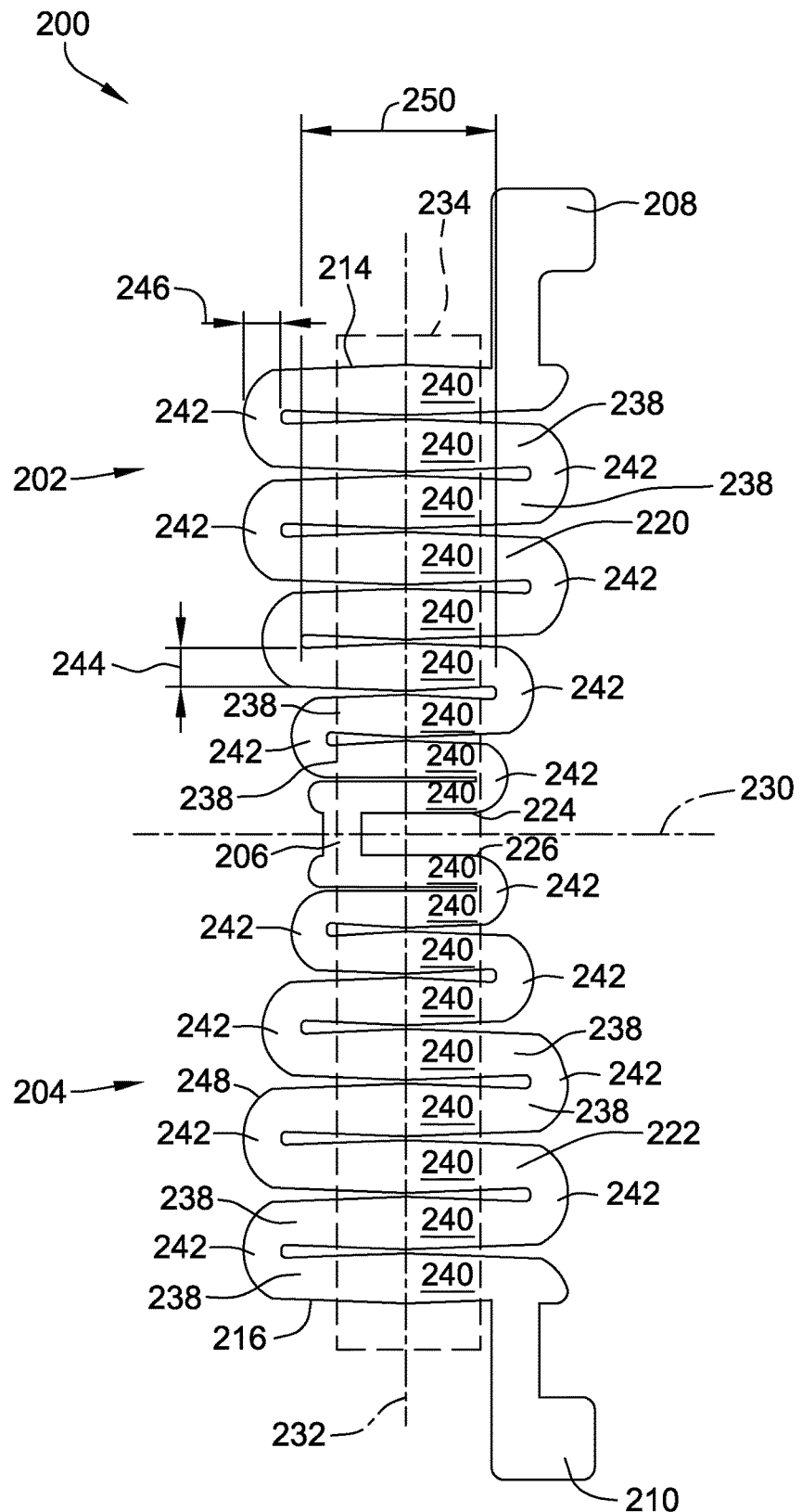
FIG. 4 is a schematic illustration of the exemplary flash heater element shown in FIG. 3.

An exemplary geometry of flash heater element 200 is shown schematically in FIG. 4. Each of first surface 202 and second surface 204 may be described with reference to a central region 234, a first axis 232 that extends along a centerline of first surface 202 and second surface 204, and a second axis 230 that is perpendicular to first axis 232. A transverse width 250, measured parallel to second axis 230, also may be defined for each of first surface electrical flow path 220 and second surface electrical flow path 222.

Central region 234 may be defined as any region where heat transfer to the environment in directions tangential to respective first surface 202 and second surface 204 is relatively less significant compared to other regions of respective first surface 202 and second surface 204. In the exemplary embodiment, each of first surface 202 and second surface 204 has a length parallel to first axis 232 that is significantly greater than transverse width 250. As a result, heat loss at the periphery of first surface 202, for example, is more significant at locations outward from first axis 232 than along first surface inlet edge 214 and second edge 224. Thus, in the exemplary embodiment of FIG. 4, central region 234 is defined as encompassing a central region on both sides of first axis 232 along the entire length of first surface 202, and central region 234 is defined similarly for second surface 204. In alternative embodiments, heat loss at the periphery along first surface inlet edge 214 and/or second edge 224 is significant compared to locations outward from first axis 232, and central region 234 is defined as excluding peripheral regions adjacent to first surface inlet edge 214 and/or second edge 224.

It should be noted that, in the embodiment of FIG. 4, first connecting tab 208, first surface 202, bridge tab 206, second surface 204, and second connecting tab 210 are illustrated as being in a longitudinally aligned, co-planar configuration for ease of explanation. Additionally, in one embodiment, FIG. 4 represents an as-manufactured configuration of a unitarily formed flash heater element 200, and flash heater element 200 may then be folded into an operational configuration to create interior region 218 as shown in FIG. 3. However, in alternative embodiments, first surface 202 and second surface 204 are not formed unitarily and/or are not formed in a co-planar fashion. Thus, in alternative embodiments, first surface 202 and second surface 204 may each have a separate respective central region 234, first axis 232 and second axis 230.

In the exemplary embodiment, each of first surface electrical flow path 220 and second surface electrical flow path 222 includes a plurality of central portions 240 each disposed at least partially within central region 234. In addition, each of first surface electrical flow path 220 and second surface electrical flow path 222 includes a plurality of peripheral sections 238 each disposed peripherally outwardly from central region 234. In certain embodiments, a width 244 of first surface electrical flow path 220 is greater within at least a portion of central portions 240 than within peripheral portions 238. Because a decreased electrical flow path width 244 corresponds to a higher resistance, more power per unit of electrical flow path length is dissipated by peripheral portions 238 than by central portions 240, and hence more heat per unit of electrical flow path length is generated by peripheral portions 238 than by central portions 240. Thus, certain embodiments counteract a tendency for a large temperature gradient to develop between a relatively hotter center of a flash heater element and a relatively cooler periphery of the element due to the peripheral edges of the heating element being free to transfer heat to the environment in directions both normal to the surface and tangential to the surface.

In some embodiments, the width 244 of each central portion 240 tapers from a maximum near first axis 232 toward a minimum near peripheral portion 238. In the particular embodiment illustrated in FIG. 4, the width 244 of each central portion 240 tapers linearly from first axis 232 toward each peripheral portion 238. In alternative embodiments, the width 244 of each central portion 240 decreases away from first axis 232 in non-linear fashion.

In the exemplary embodiment shown in FIG. 4, each central portion 240 extends generally parallel to second axis 230 across first axis 232, and each peripheral portion 238 is connected to a respective end, disposed outwardly from first axis 232, of one of the plurality of central portions 240. Each of first surface electrical flow path 220 and second surface electrical flow path 222 further includes a plurality of connecting portions 242. Connecting portions 242 connect the plurality of central portions 240 and the plurality of peripheral portions 238 in series in serpentine fashion. More specifically, each connecting portion 242 connects a peripheral portion 238 at the end of one central portion 240 to a peripheral portion 238 at the end of an adjacent central portion 240.

Moreover, in certain embodiments, such as the embodiment illustrated in FIG. 4, an electrical flow path width 246 within at least a portion of each connecting portion 242 is less than or equal to the electrical flow path width 244 of an adjacent peripheral portion 238. Again, because a decreased electrical flow path width corresponds to a higher resistance, more power per unit of electrical flow path length is dissipated by such a connecting portion 242 than by central portions 240, and hence more heat per unit of electrical flow path length is emitted by such a connecting portion 242 than by central portions 240. In addition, in the exemplary embodiment, connecting portions 242 each have arcuate, rather than rectangular or linear, peripheral edges 248 to provide more uniform heating at edges 248. In a particular embodiment, the decrease in electrical flow path width 244 within peripheral portions 238 and/or the decrease in electrical flow path width 246 within connecting portions 242, relative to electrical flow path width 244 near first axis 232, results in approximately 25 percent less conductive cross-sectional area outside central region 234 than within central region 234. In another particular embodiment, a ratio of width 244 at a first location in at least one central portion 240 to width 244 of a second location in the at least one central portion 240 is approximately equal to a ratio of a temperature at the first location to a temperature at the second location in an otherwise-identical flash heater element having constant electrical flow path width (not shown).

Figure 5:
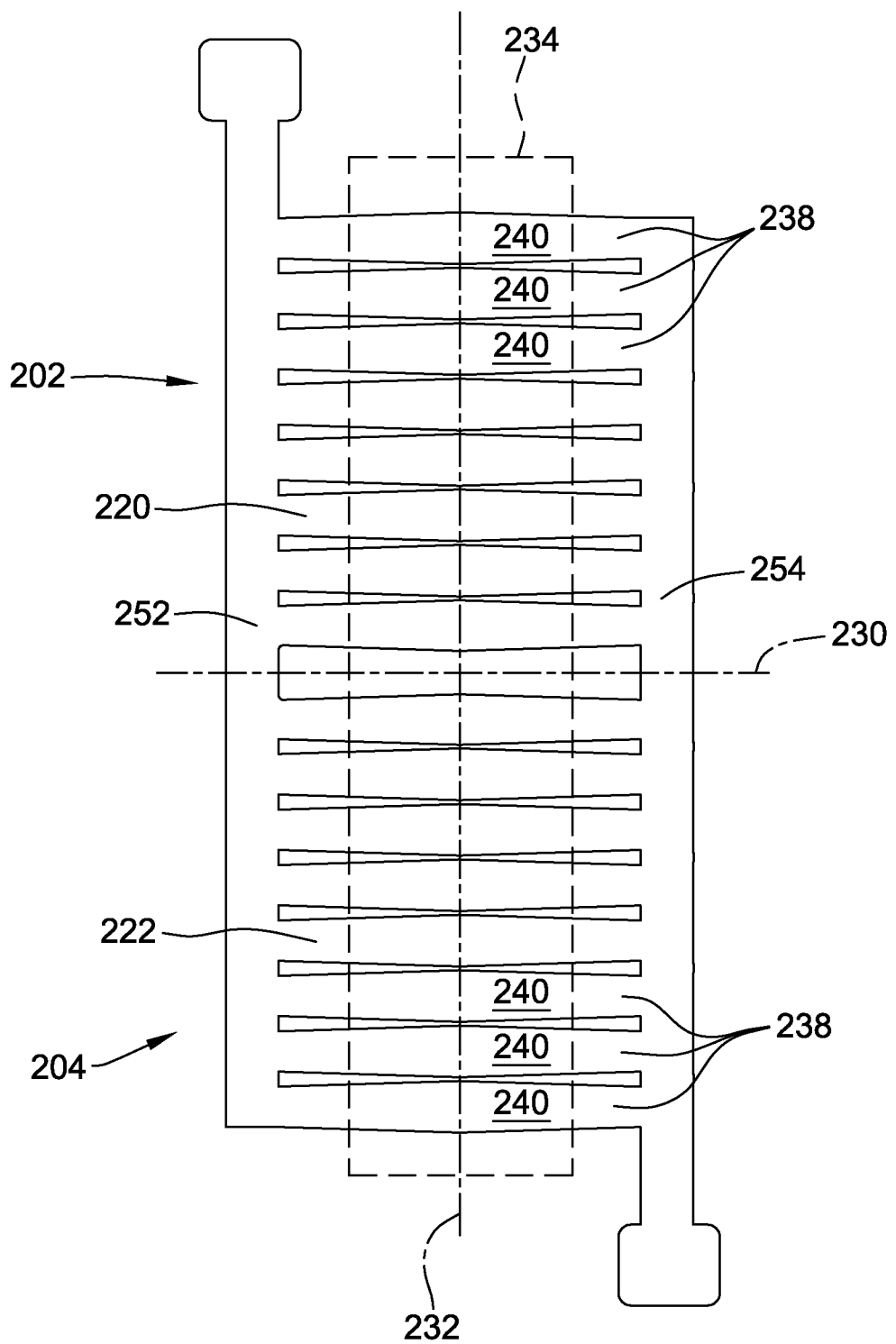
FIG. 5 is a schematic illustration of an alternative embodiment of a flash heater element that may be used with the exemplary detection system shown in FIG. 1 and FIG. 2.

In alternative embodiments, one or both of electrical flow path 220 and electrical flow path 222 are completed in a fashion other than by the use of connecting portions 242. For example, in the alternative embodiment illustrated in FIG. 5, the plurality of central portions 240 are connected in parallel by a bus line 252 and a bus line 254, each connected in parallel to the peripheral portions 238 on a respective side of first surface 202 and second surface 204.

It also should be noted that varying electrical flow path width 244 to adjust the temperature gradient on first surface 202 and second surface 204 is not limited to facilitating a uniform temperature distribution. For example, with reference to FIG. 3, in certain embodiments it is desirable to produce a hotter temperature on first surface 202 and second surface 204 near inlet 212 to compensate for an inflow of relatively colder air through slot 132 (shown in FIG. 2). In such circumstances, the embodiment shown in FIG. 4, for example, may be altered by reducing electrical flow path width 244 for at least a portion of central portions 240 adjacent first surface inlet edge 214 and second surface inlet edge 216 relative to central portions 240 that are not adjacent first surface inlet edge 214 or second surface inlet edge 216, causing a corresponding temperature increase at those locations. In alternative embodiments, a non-uniform temperature gradient is desired at a predetermined location on first surface 202 and/or second surface 204, and electrical flow path width 244 is increased at the predetermined location to cause a corresponding desired temperature decrease, or alternatively electrical flow path width 244 is decreased at the predetermined location to cause a corresponding desired temperature increase, when flash heater element 200 is activated.

Returning to the embodiment illustrated in FIG. 4, transverse width 250 decreases near respective second edges 224 and 226. When flash heater element 200 is configured for operation, as shown in FIG. 3, this decrease in transverse width 250 results in a tapering of flash heater element 200 toward second end 228 opposite inlet 212. With reference also to FIG. 2, this tapering of transverse width 250 toward second end 228 facilitates uniform heating within desorber receptacle 126 in embodiments where a width (not shown) of desorber receptacle 126, measured in a transverse direction 128, tapers toward an end 134 of desorber 112 that is adjacent to detector 114. When flash heater element 200 is installed in desorber 112, transverse direction 128 is parallel to second axis 230.

Figure 6:
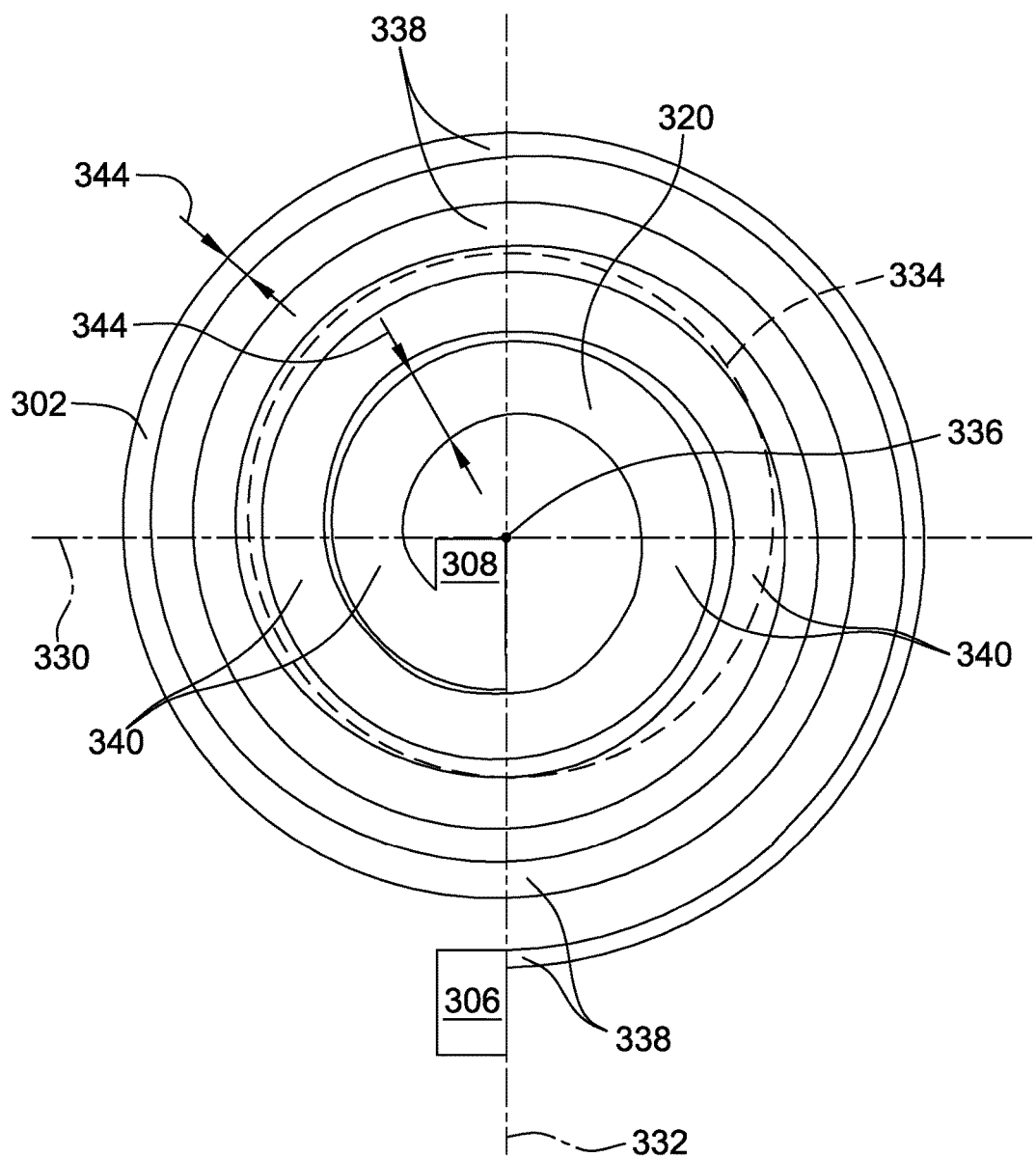
FIG. 6 is a schematic illustration of an alternative embodiment of a flash heater element first surface that may be used with the exemplary detection system shown in FIG. 1 and FIG. 2.

An alternative embodiment of a geometry for a first surface 302 of flash heater element 200 is shown schematically in FIG. 6. First surface 302 includes an electrical flow path 320 that follows a generally spiral path between a first connecting tab 308 and a bridge tab 306. First surface 302 may be described with reference to a central region 334, a first axis 332 and a second axis 330 that is parallel to first axis 332. In contrast to the embodiment shown in FIG. 4, first surface 302 has no significant difference in a length measured parallel to first axis 332 compared to a length measured parallel to second axis 330. As a result, heat loss is relatively significant at all locations of a periphery of first surface 302, and central region 334 is defined as an approximately circular region around a central point 336 of first surface 302.

First surface electrical flow path 320 includes a plurality of central portions 340 each disposed at least partially within central region 334. In addition, first surface electrical flow path 320 includes a plurality of peripheral sections 338 each disposed peripherally outwardly from central region 334. In certain embodiments, a width 344 of first surface electrical flow path 320 is greater within at least a portion of central portions 340 than within peripheral portions 338. Because a decreased electrical flow path width 344 corresponds to a higher resistance, more power per unit of electrical flow path length is dissipated by peripheral portions 338 than by central portions 340, and hence more heat per unit of electrical flow path length is generated by peripheral portions 338 than by central portions 340. Thus, certain embodiments again counteract a tendency for a large temperature gradient to develop between a relatively hotter center of a flash heater element and a relatively cooler periphery of the element due to the peripheral edges of the heating element being free to transfer heat to the environment in directions both normal to the surface and tangential to the surface.

In a particular embodiment, the decrease in electrical flow path width 344 within peripheral portions 338, relative to electrical flow path width 344 within central portions 340, results in approximately 25 percent less conductive cross-sectional area outside central region 334 than within central region 334. In another particular embodiment, a ratio of width 344 at a first location in at least one central portion 340 to width 344 of a second location in the at least one central portion 340 is approximately equal to a ratio of a temperature at the first location to a temperature at the second location in an otherwise-identical heating element having constant electrical flow path width (not shown).

In other alternative embodiments, flash heater element 200 includes at least one surface with an electrical flow path geometry other than a serpentine or spiral flow path. For example, in an alternative embodiment (not shown), a single surface of flash heater element 200 includes adjacent serpentine or rectangularly spiraled electrical flow paths connected in series or in parallel. Each of these alternative embodiments includes a central region where heat transfer to the environment in directions tangential to the surface is relatively less significant compared to other regions of the surface, and in each such embodiment, a width of the electrical flow path is greater within at least a portion of a central portion than within a peripheral portion of the electrical flow path.

Figure 7:
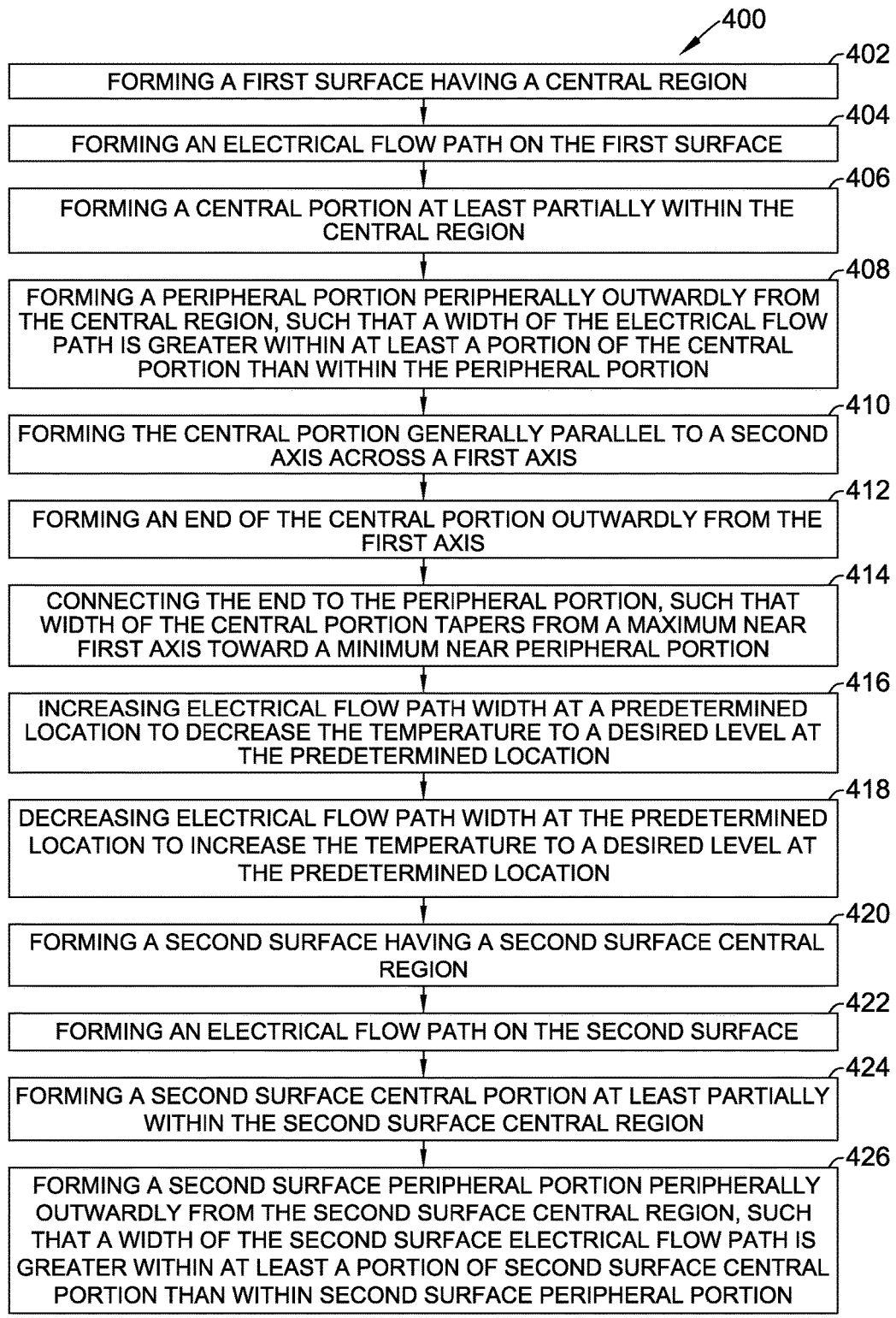
FIG. 7 is a flow diagram of an exemplary method of making a flash heater element.

An exemplary method 400 for making a flash heater element is illustrated in FIG. 7. Exemplary method 400 includes forming 402 a first surface, such first surface 202, having a central region, for example central region 234. Exemplary method 400 also includes forming 404 an electrical flow path, for example electrical flow path 220, on the first surface. Forming the electrical flow path comprises forming 406 a central portion, such as central portion 240, at least partially within the central region, and forming 408 a peripheral portion, such as peripheral portion 238, peripherally outwardly from the central region, such that a width 244 of the electrical flow path is greater within at least a portion of the central portion than within the peripheral portion.

In the exemplary method 400, forming 406 the central portion further includes, where the central region is defined along a first axis such as first axis 232, the first surface having a second axis 230 perpendicular to first axis 232, forming 410 the central portion generally parallel to the second axis across the first axis. Exemplary method 400 further includes forming 412 an end of central portion 240 outwardly from first axis 232, and connecting 414 the end to peripheral portion 238, such that width 244 of central portion 240 tapers from a maximum near first axis 232 toward a minimum near peripheral portion 238. In the exemplary method 400, forming 404 an electrical flow path further comprises one of (i) increasing 416 electrical flow path width 244 at a predetermined location to decrease the temperature to a desired level at the predetermined location when flash heater element 200 is activated, and (ii) decreasing 418 the electrical flow path width at the predetermined location to increase the temperature to a desired level at the predetermined location when flash heater element 200 is activated.

Additionally, exemplary method 400 includes forming 420 a second surface, such as second surface 204, having a second surface central region, and forming 422 an electrical flow path on the second surface. In the exemplary method 400, forming 422 the second surface electrical flow path includes forming 424 a second surface central portion, such as central portion 240, at least partially within the second surface central region, and forming 426 a second surface peripheral portion, such as peripheral portion 238, peripherally outwardly from the second surface central region, such that a width 244 of the second surface electrical flow path is greater within at least a portion of second surface central portion 240 than within second surface peripheral portion 238.

Exemplary embodiments of a flash heater element that provides uniform heating are described in detail above. The above-described embodiments are configured to increase the temperature of a target area from a first temperature to a second temperature within a time period of just a few seconds. The above-described embodiments facilitate a uniform temperature distribution at the second temperature. Moreover, the above-described embodiments facilitate a more uniform temperature distribution not by seeking to limit the effect of "current crowding" at peripheral portions, but rather by utilizing the effect of "current crowding" to advantage. The above-described embodiments alternatively facilitate a desired non-uniform temperature gradient. When employed in a desorber of a detection system, the above-described embodiments facilitate consistent vaporization of trace particles from all locations on a sampling device within an expected time period, resulting in an increased quality and consistency of trace particle detection. Moreover, the above-described embodiments avoid an increased cost, internal complexity, system size, time, and power requirement that would occur if a second desorber were required in a detection system to enable consistent vaporization at the second temperature. Thus, the above-described embodiments provide a significant advantage over existing technologies.

Although the foregoing description contains many specifics, these should not be construed as limiting the scope of the present disclosure, but merely as providing illustrations of some of the presently preferred embodiments. Similarly, other embodiments may be devised which do not depart from the spirit or scope of the present disclosure. Features from different embodiments may be employed in combination. For example, components of each system and/or steps of each method may be used and/or practiced independently and separately from other components and/or steps described herein. In addition, each component and/or step may also be used and/or practiced with other assemblies and methods. The scope of the disclosure is, therefore, indicated and limited only by the appended claims and their legal equivalents, rather than by the foregoing description.

While the invention has been described in terms of various specific embodiments, those skilled in the art will recognize that the invention can be practiced with modification within the spirit and scope of the claims. Although specific features of various embodiments of the invention may be shown in some drawings and not in others, this is for convenience only. Moreover, references to "one embodiment" in the above description are not intended to be interpreted as excluding the existence of additional embodiments that also incorporate the recited features. In accordance with the principles of the invention, any feature of a drawing may be referenced and/or claimed in combination with any feature of any other drawing.

What is claimed is:
1. A flash heater element comprising:
   a first surface and an oppositely disposed second surface, wherein a first axis is defined along a centerline of each of said first and second surfaces and a second axis is defined perpendicular to said first axis, said second surface is parallel to said first surface and offset from said first surface along a third axis perpendicular to said first and second axes, said first and second surfaces connected by a bridge tab, and wherein each of said first and second surfaces comprises:
      a plurality of central portions disposed in series along said first axis, each said central portion extends between a respective pair of peripheral portions in a direction generally parallel to said second axis across said first axis, wherein an electrical flow path width of each said central portion tapers linearly from said first axis toward each of said pair of peripheral portions; and
      a plurality of connecting portions that connect said plurality of central portions in series in serpentine fashion.
2. A flash heater element in accordance with claim 1, wherein a width of said central portion tapers from a maximum near the first axis toward a minimum near said peripheral portion.

3. A flash heater element in accordance with claim 2, wherein an electrical flow path width within said connecting portions is less than or equal to said electrical flow path width of said central portions at said peripheral portion.

4. A flash heater element in accordance with claim 1, said first surface further comprising an inlet edge, wherein said electrical flow path width is reduced for one of said central portions adjacent said inlet edge relative to another of said central portions that is not adjacent said inlet edge.

5. A flash heater element in accordance with claim 1, said electrical flow path further comprises a predetermined location, said electrical flow path width at said predetermined location is one of (i) increased to cause a corresponding desired temperature decrease at said predetermined location, and (ii) decreased to cause a corresponding desired temperature increase at said predetermined location.

6. A flash heater element in accordance with claim 1, further comprising a bridge tab connecting said first surface and said second surface in series.

7. A flash heater element in accordance with claim 1, wherein said first surface and said second surface are configured for operable coupling to separate electrical circuits.

8. A flash heater element in accordance claim 1, wherein said connecting portions each have arcuate peripheral edges.

9. A detection system for identifying trace particles using thermal desorption, said detection system comprising:
a housing comprising a slot configured to receive a sampling device;
a desorber disposed within said housing proximate said slot, said desorber comprising a receptacle aligned with said slot, said receptacle configured to receive at least a portion of the sampling device;
at least one heater disposed within said housing external to said receptacle, said at least one heater operable to maintain said receptacle at a first temperature such that, when the sampling device is inserted into said receptacle, a first class of trace particles collected on the sampling device is vaporized;
a flash heater element configured to increase a temperature of said receptacle to a second temperature such that a second class of trace particles collected on the sampling device is vaporized, said flash heater element comprising a first surface that at least partially defines a first side of said receptacle and a second surface that at least partially defines an opposite second side of said receptacle, wherein a first axis is defined along a centerline of each of said first and second surfaces and a second axis is defined perpendicular to said first axis, said second surface is parallel to said first surface and offset from said first surface along a third axis perpendicular to said first and second axes, said first and second surfaces connected by a bridge tab, and wherein each of said first and second surfaces comprises:
a plurality of central portions disposed in series along said first axis, each said central portion extends between a respective pair of peripheral portions in a direction generally parallel to said second axis across said first axis, wherein an electrical flow path width of each said central portion tapers linearly from said first axis toward each of said pair of peripheral portions; and
a plurality of connecting portions that connect said plurality of central portions in series in serpentine fashion; and
a detector disposed within said housing in flow communication with said desorber, said detector is configured to receive and identify the vaporized first class of trace particles and the vaporized second class of trace particles.

10. A detection system in accordance with claim 9, further comprising an electronics assembly operatively coupled to said desorber and said detector.

11. A detection system in accordance with claim 10, wherein said electronics assembly is programmed to operate said flash heater to increase the temperature within said receptacle to each of a plurality of temperatures in sequence, such that a corresponding one of a plurality of classes of substances is vaporized at each temperature.

12. A detection system in accordance with claim 10, further comprising a user interface operatively coupled to said electronics assembly, said user interface configured to allow a user to input commands into, and view results from, said detection system.

13. A detection system in accordance with claim 9, wherein a width of said central portion tapers from a maximum near the first axis toward a minimum near said peripheral portion.

14. A detection system in accordance claim 9, wherein said connecting portions each have arcuate peripheral edges.

15. A method of making a flash heater element, said method comprising:
forming a first surface and an oppositely disposed second surface, wherein a first axis is defined along a centerline of each of the first and second surfaces and a second axis is defined perpendicular to the first axis, the second surface is parallel to the first surface and offset from the first surface along a third axis perpendicular to the first and second axes, the first and second surfaces connected by a bridge tab, and wherein each of the first and second surfaces includes:
a plurality of central portions disposed in series along the first axis, each central portion extends between a respective pair of peripheral portions in a direction generally parallel to the second axis across the first axis, wherein an electrical flow path width of each central portion tapers linearly from the first axis toward each of the pair of peripheral portions; and
a plurality of connecting portions that connect the plurality of central portions in series in serpentine fashion.

16. A method in accordance with claim 15, wherein said forming the first and second surfaces further comprises forming first and second surfaces
such that a width of the central portion tapers from a maximum near the first axis toward a minimum near the peripheral portion.

17. A method in accordance with claim 15, wherein said forming the first and second surfaces further comprises one of (i) increasing the electrical flow path width at a predetermined location to decrease the temperature to a desired level at the predetermined location when the flash heater element is activated, and (ii) decreasing the electrical flow path width at the predetermined location to increase the temperature to a desired level at the predetermined location when the flash heater element is activated.

18. A method in accordance with claim 15, wherein said forming the first and second surfaces further comprises
forming the first and second surfaces such that a width of the electrical flow path within the connecting portions is less than or equal to the width of the electrical flow path of the central portions at the peripheral portion.

19. A method in accordance claim 15, wherein said forming the first and second surfaces further comprises forming the first and second surfaces such that the connecting portions each have arcuate peripheral edges.

* * * * *